(12) United States Patent
Freudenberger et al.

(10) Patent No.: US 10,537,294 B2
(45) Date of Patent: Jan. 21, 2020

(54) X-RAY DEVICE FOR INVERSE COMPUTER TOMOGRAPHY

(71) Applicant: Siemens Healthcare GmbH, Erlangan (DE)

(72) Inventors: Joerg Freudenberger, Kalchreuth (DE); Peter Roehrer, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 185 days.

(21) Appl. No.: 15/741,815

(22) PCT Filed: May 19, 2016

(86) PCT No.: PCT/EP2016/061260
§ 371 (c)(1),
(2) Date: Jan. 4, 2018

(87) PCT Pub. No.: WO2017/008938
PCT Pub. Date: Jan. 19, 2017

(65) Prior Publication Data
US 2018/0192968 A1    Jul. 12, 2018

(30) Foreign Application Priority Data
Jul. 15, 2015    (DE) .................. 10 2015 213 285

(51) Int. Cl.
*A61B 6/03*    (2006.01)
*A61B 6/06*    (2006.01)
*A61B 6/00*    (2006.01)

(52) U.S. Cl.
CPC ............... *A61B 6/035* (2013.01); *A61B 6/06* (2013.01); *A61B 6/44* (2013.01)

(58) Field of Classification Search
CPC .... A61B 6/00; A61B 6/03; A61B 6/06; A61B 6/035; A61B 6/44; A61B 6/032; A61B 6/4007; A61B 6/4488; H05G 1/02
(Continued)

(56) References Cited

U.S. PATENT DOCUMENTS

2004/0114721 A1    6/2004    Qiu
2005/0226364 A1    10/2005   De Man
(Continued)

FOREIGN PATENT DOCUMENTS

DE    102004056094 A1    6/2005
DE    102008050352 A1    4/2010
(Continued)

OTHER PUBLICATIONS

Baek, Jongduk et al.: "A multi-source inverse-geometry CT system: initial results with an 8 Spot x-ray source array"; in: Phys. Med. Biol.; vol. 59, No. 5; pp. 1189-1202; 2014; DOI 10.1088/0031-9155/59/5/1189; XP-Nr. 20257847A.
(Continued)

*Primary Examiner* — Jurie Yun
(74) *Attorney, Agent, or Firm* — Harness, Dickey & Pierce, P.L.C.

(57) ABSTRACT

An X-ray device for an inverse computer tomography configuration, includes a plurality of X-ray emitters and a detector arranged opposite the X-ray emitters. The X-rays emitted by the X-ray emitters can be detected by the detector after at least partly passing through an examination region located in the intermediate region between the X-ray emitters and the detector. In an embodiment, the X-ray emitters are grouped into at least two mutually spaced sub-arrangements. Each sub-arrangement comprises multiple X-ray emitters. The spacing between the at least two sub-arrange-
(Continued)

ments is greater than the spacing between adjacent X-ray emitters of at least one of the sub-arrangements.

20 Claims, 2 Drawing Sheets

(58) Field of Classification Search
USPC .................... 378/4, 9, 10, 12, 119, 124, 147
See application file for complete search history.

(56) References Cited

U.S. PATENT DOCUMENTS

| | | |
|---|---|---|
| 2007/0223650 A1 | 9/2007 | Francke |
| 2007/0258562 A1 | 11/2007 | Dinca et al. |
| 2010/0091938 A1 | 4/2010 | Fadler |
| 2011/0280367 A1 | 11/2011 | Baeumer |
| 2014/0226787 A1 | 8/2014 | Utsumi |

FOREIGN PATENT DOCUMENTS

| | | |
|---|---|---|
| DE | 102009007857 A1 | 5/2010 |
| EP | 2378974 B1 | 4/2013 |
| WO | WO 2011000784 A1 | 1/2011 |
| WO | WO 2014047518 A1 | 3/2014 |
| WO | WO 2014138500 A1 | 9/2014 |

OTHER PUBLICATIONS

Hsieh, Scott S. et al.: "The feasibility of an inverse geometry CT system with stationary source arrays"; in: Medical Physics; vol. 40, No. 3; pp. 31904-1-31904-14; ISSN 0094-2405; DOI 10.1118/1.4789918; XP-Nr. 012171044, Mar. 2013.

International Search Report PCT/ISA/210 for International Application No. PCT/EP2016/061260 dated Aug. 23, 2016. 0.

Written Opinion of the International Searching Authority PCT/ISA/237 for International Application No. PCT/EP2016/061260 dated Aug. 23, 2016.

German Office Action for German Application No. 102015213285.4, dated Mar. 11, 2016.

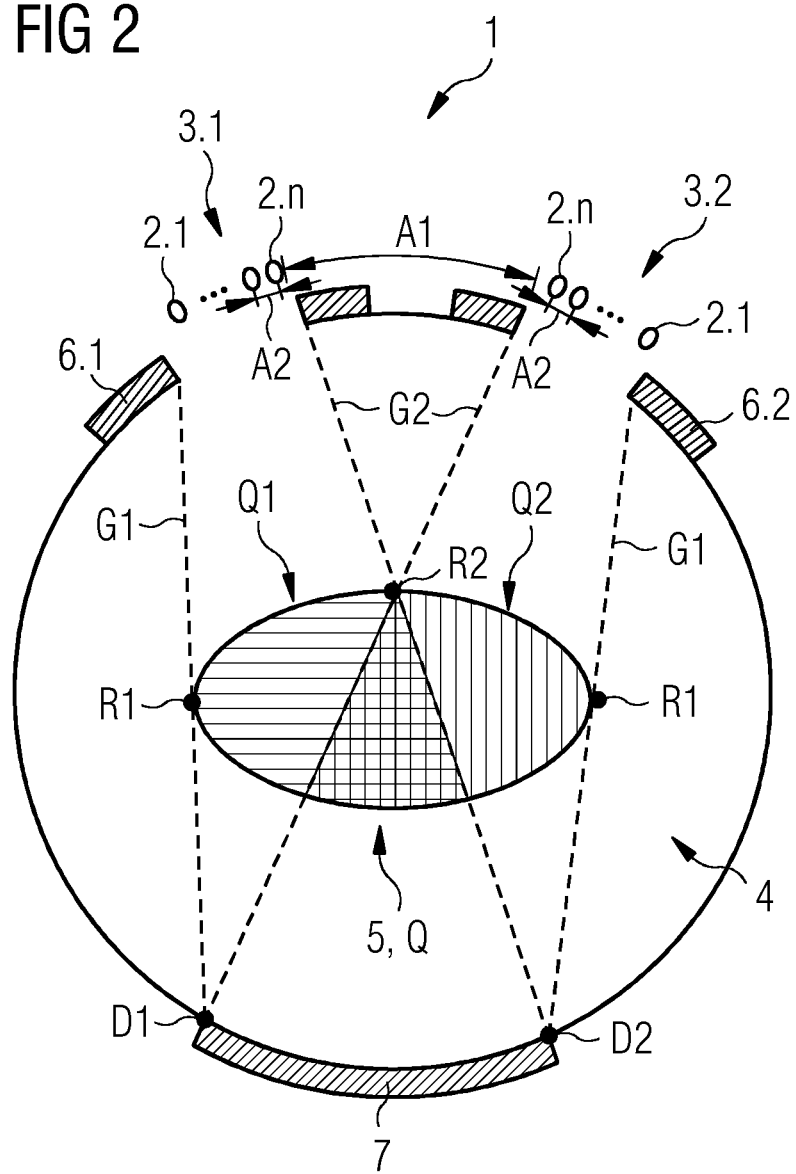

X-RAY DEVICE FOR INVERSE COMPUTER TOMOGRAPHY

PRIORITY STATEMENT

This application is the national phase under 35 U.S.C. § 371 of PCT International Application No. PCT/EP2016/061260 which has an International filing date of May 19, 2016, which designated the United States of America and which claims priority to German patent application number DE 102015213285.4 filed Jul. 15, 2015, the entire contents of which are hereby incorporated herein by reference.

FIELD

An embodiment of invention generally relates to an X-ray device for inverse computed tomography, having a plurality of X-ray emitters and/or to a detector arranged opposite the X-ray emitters. After passing through at least some of a region of interest located in the intermediate region between the X-ray emitters and the detector, the X-rays emitted by the X-ray emitters can be detected by the detector.

BACKGROUND

In the case of tomographic X-ray imaging, such as in particular computed tomography or tomosynthesis, an object undergoing examination must be irradiated from various directions so that a three-dimensional image data set can be generated. This is typically done using an X-ray emitter, which can broadly speaking be regarded as a point source of X-rays, and a relatively large detector. The X-ray emitter and the detector are rotated about the object undergoing examination for the purpose of acquiring image data.

Further, X-ray devices have been developed in which the detector is made smaller for cost reasons. In configurations of this kind, however, generally speaking it is no longer possible to illuminate or irradiate the entire region of interest that is to be acquired using only a single X-ray emitter.

For this reason, EP 2 378 974 B1 proposes an X-ray device for so-called inverse computed tomography in which there is provided only one detector, with a relatively small detector surface. For the purpose of irradiating the region of interest, a plurality of X-ray emitters are provided in an arrangement equidistant from one another. The X-ray emitters may be connected up sequentially, individually or in groups.

SUMMARY

At least one embodiment of the present invention provides an improved X-ray device that is optimized in particular in respect of the output required of the X-ray emitters.

According to at least one embodiment of the invention, an X-ray device is disclosed.

Advantageous embodiments of the invention form the subject matter of the claims.

An X-ray device for inverse computed tomography, of at least one embodiment, includes a plurality of X-ray emitters and a detector arranged opposite the X-ray emitters. After passing through at least some of a region of interest located in the intermediate region between the X-ray emitters and the detector, the X-rays emitted by the X-ray emitters can be detected by the detector.

According to at least one embodiment of the invention, the X-ray emitters are grouped, in an arrangement other than equidistant from one another, into at least two mutually spaced sub-arrangements, wherein each sub-arrangement includes a plurality of X-ray emitters. A spacing between the at least two sub-arrangements is greater than a spacing between adjacent X-ray emitters of at least one of the sub-arrangements.

BRIEF DESCRIPTION OF THE DRAWINGS

For a further description of the invention, the reader is referred to the example embodiments shown in the figures of the drawings. Here, in a schematic sketch illustrating the principle:

FIG. 2 shows a sectional illustration of X-ray radiation according to another example embodiment, with an arcuate arrangement of X-ray emitters.

Mutually corresponding parts are provided with the same reference numerals in all figures.

DETAILED DESCRIPTION OF THE EXAMPLE EMBODIMENTS

Figure 1:
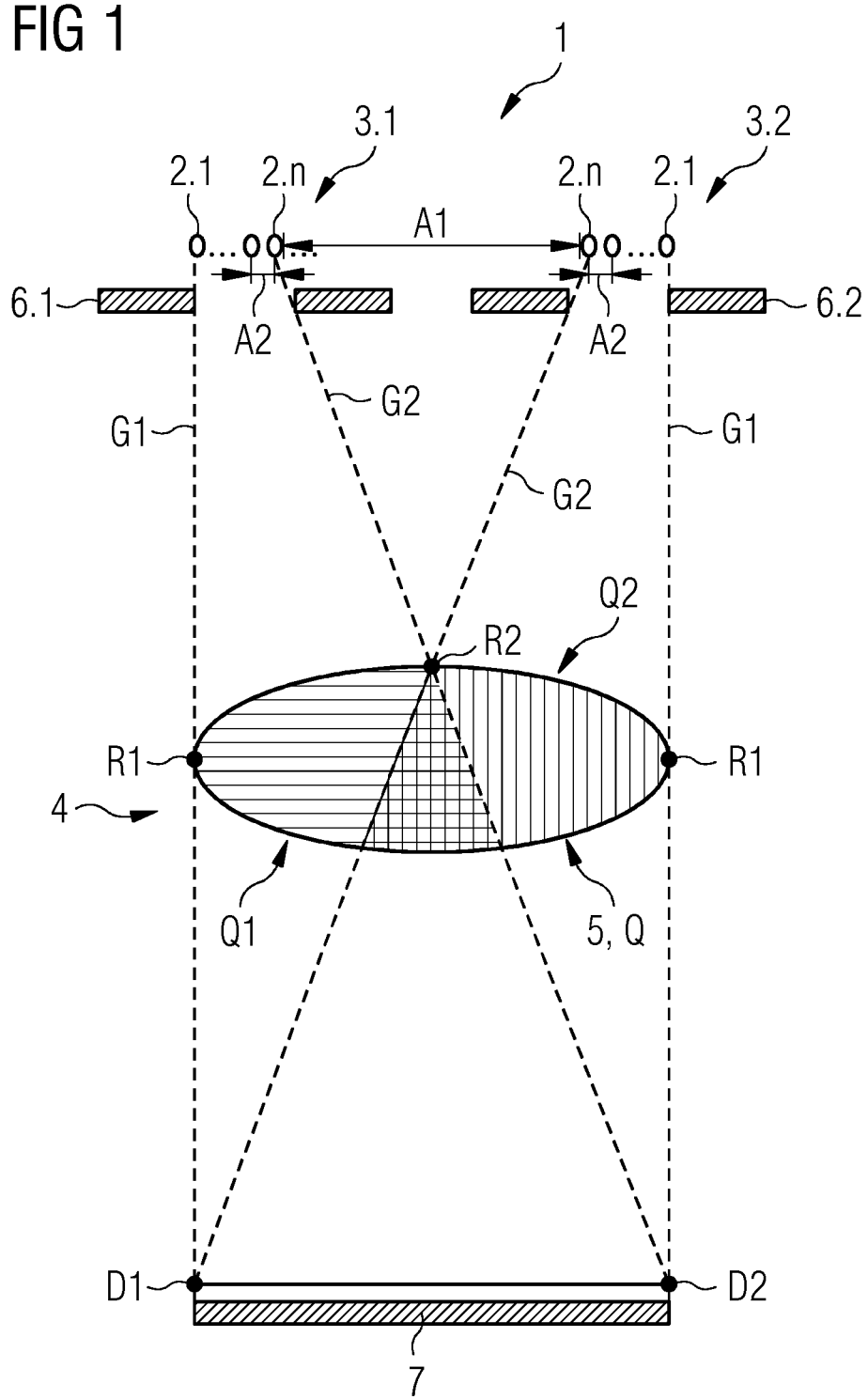
FIG. 1 shows a sectional illustration of the X-ray device according to an example embodiment of the invention, with a linear arrangement of X-ray emitters.

An X-ray device for inverse computed tomography, of at least one embodiment, includes a plurality of X-ray emitters and a detector arranged opposite the X-ray emitters. After passing through at least some of a region of interest located in the intermediate region between the X-ray emitters and the detector, the X-rays emitted by the X-ray emitters can be detected by the detector.

According to at least one embodiment of the invention, the X-ray emitters are grouped, in an arrangement other than equidistant from one another, into at least two mutually spaced sub-arrangements, wherein each sub-arrangement includes a plurality of X-ray emitters. A spacing between the at least two sub-arrangements is greater than a spacing between adjacent X-ray emitters of at least one of the sub-arrangements.

The following observation is a basis for at least one embodiment of the invention: in configurations that have a detector surface that is smaller than conventional arrangements, a plurality of X-ray emitters have to be provided for the purpose of irradiating the region of interest, since only the solid angle region that can be irradiated by the respective X-ray emitter, and which is also detected by the detector, can be utilized for the image acquisition. As a result, generally speaking, the smaller the detector surface of the detector is chosen to be, the more X-ray emitters must thus be provided.

However, read-out of the detector must be performed after each irradiation. This means that, for an exposure, in order to give approximately the same signal-to-noise ratio each X-ray emitter of a linear and approximately equidistant arrangement would have to emit approximately the same number of photons as the single X-ray emitter of a conventional X-ray device. However, for the purpose of capturing a projection, a number of exposures that corresponds to the number of X-ray emitters is required. On the assumption that capture of a projection is to be performed at least approximately within the same length of time, it follows that with an approximately equidistant arrangement of X-ray emitters the intensity to be emitted by each of the X-ray emitters must be increased, approximately by a factor corresponding to the number of X-ray emitters. This has direct consequences not only for the high-voltage generator for the X-ray emitters, the output whereof must be increased by a corresponding factor, but also for the detector, for which read-out must be faster by the corresponding factor.

At this point it should also be noted that, at least in the field of medical applications, there is a limit to the extent by which the exposure times can be made longer, because of the disruptive movement of organs, which leads to image artifacts.

It has been realized that the higher requirements described above in respect of the output of the high-voltage generator occur only to a lesser extent in the case of a one-dimensional and non-equidistant arrangement of X-ray emitters.

According to at least one embodiment of the invention, it is thus proposed that the X-ray emitters should be grouped into at least two sub-arrangements. In this case, each of the sub-arrangements irradiates substantially one volume of the region of interest, the volumes being of the same size. For this purpose, the X-ray emitters are in a spatially dense arrangement within the respective sub-arrangements. The sub-arrangements are arranged at a spacing from one another that is greater than a spacing between adjacent X-ray emitters in at least one of the sub-arrangements.

It has been shown that, with an arrangement of this kind, the output requirements of the individual X-ray emitters and hence also of the high-voltage generator for the X-ray emitters are markedly reduced. The high-voltage generator can be of smaller size than in other inverse constructions that seek to achieve an unchanged exposure time by comparison with conventional projection imaging. In this case, the size depends both on the number of sub-groups into which the X-ray emitters are grouped and also on the exposure time sought. Assuming an exposure time as in the case of a conventional arrangement, in which only one X-ray emitter illuminates a detector, and ignoring electronic noise during read-out of the detector, if for example there is grouping into two sub-groups the high-voltage generator need only deliver approximately twice the output by comparison with the conventional arrangement. The high-voltage generator can accordingly be of smaller size. Moreover, it becomes possible to use X-ray emitters with stationary anodes, since the intensity to be emitted by the X-ray emitters remains below a critical threshold value at which heat damage to the anode could be expected.

All the X-ray emitters are arranged next to one another in a row. Since the spacing between the sub-groups themselves is greater than the spacing between the X-ray emitters in at least one of the sub-groups, this means that not all the X-ray emitters are arranged equidistant from one another. According to preferred example embodiments, the X-ray emitters are arranged in a linear row or on a circular path.

Preferably, the region that can be irradiated by the X-ray emitters of the respective sub-arrangement is limited to a partial region of a maximum cross-sectional area of the region of interest that can be irradiated. The partial regions, taken in their entirety, completely cover the cross-sectional area of the region of interest.

In a concrete example embodiment, each of the partial regions is delimited at its margin by a first and a second straight line, wherein the first straight line runs through a side edge of the detector, a lateral marginal point that laterally delimits the cross-sectional area, and an X-ray emitter of the associated sub-arrangement. The second straight line runs through a further, opposite side edge of the detector, an upper marginal point that upwardly delimits the cross-sectional area, and a further X-ray emitter of the associated sub-arrangement.

The second straight lines of the at least two sub-arrangements of this example embodiment preferably intersect at the upper marginal point.

Preferably, the first straight lines that are associated with the at least two sub-arrangements run approximately parallel to one another. In a development of the invention, it is thus provided for the X-ray emitters to be spatially arranged such that the first straight lines of the at least two sub-arrangements run at an angle of less than 30° to one another.

Particularly preferably, associated with each sub-arrangement is a respective collimator that limits the path of radiation accordingly to a corresponding partial region of the region of interest.

The X-ray emitters that are grouped in the sub-arrangements are preferably arranged linearly within the associated sub-arrangement.

Particularly preferably, the X-ray emitters that are grouped in the sub-arrangements are arranged to be equidistant from one another within the associated sub-arrangement.

In an example embodiment, exactly two sub-arrangements are provided and are arranged such that the region of interest can be irradiated completely by the X-ray emitters of the two sub-arrangements taken in their entirety. In a suitable arrangement of the X-ray emitters and the sub-arrangements, the increased output requirement made of the X-ray emitters in respect of the intensity to be emitted may, in an ideal case, be limited to a factor of only approximately two in relation to a conventional X-ray device having only one X-ray source. In embodiments of this kind, the two sub-arrangements each irradiate approximately half the volume of the region of interest.

In an example embodiment, the at least two sub-arrangements and the detector are arranged peripherally around a tunnel-like examination chamber. An embodiment of this kind may in particular correspond to an inverse geometry computed tomography device. In another example embodiment, the X-ray emitters are arranged to be substantially planar.

As already mentioned, and particularly advantageously, the fact that the radiation intensity is to be increased only comparatively slightly enables X-ray emitters having stationary anodes to be used. Preferably, each X-ray emitter of the at least two sub-arrangements has a stationary anode.

Particularly powerful stationary anodes are made at least partly of diamond and have a coating of tungsten. Use of anodes of this kind has proved advantageous, since ultimately the radiation intensity to be emitted by the individual X-ray emitters must always be increased by comparison with conventional X-ray devices.

Preferably, the stationary anode is embedded in copper for the purpose of better dissipation of heat. This serves to avoid heat damage to the anode, with the result that it can provide X-rays of increased intensity.

FIG. 1 shows, by way of example, a possible embodiment of the X-ray device 1 according to the invention, in a schematic sectional illustration. The X-ray device 1 includes a plurality of X-ray emitters 2.1 to 2.n that are arranged next to one another and are grouped into two sub-arrangements 3.1, 3.2.

All the X-ray emitters 2.1 to 2.n of the sub-arrangements are arranged in a row and are not all equidistant from one another, since the sub-arrangements 3.1, 3.2 are at a greater spacing A1 from one another than the spacing A2 of the X-ray emitters within the respective sub-groups 3.1, 3.2.

The X-ray emitters 2.1 to 2.n of the associated sub-arrangements 3.1, 3.2 are arranged, as seen in the illustrated plane of the drawing, in linear rows and equidistant from one another. The X-ray emitters 2.1 to 2.*n* are at a smaller spacing A2 from one another within the corresponding sub-arrangement 3.1, 3.2 than the sub-arrangements 3.1, 3.2 are from one another.

The X-ray emitters 2.1 to 2.*n* are controllable separately from one another, at least in accordance with the sub-groups 3.1, 3.2. Preferably, each of the X-ray emitters 2.1 to 2.*n* is controllable individually.

In the direction running perpendicular to the plane of the drawing, further X-ray emitters may be provided, in particular at the margins of an examination chamber 4 in a different spatial configuration.

In the examination chamber 4, which is located between the X-ray emitters 2.1 to 2.*n* and a detector 7, there is a region of interest 5 whereof the cross-sectional area Q has an approximately elliptical shape in the plane of the drawing. The X-ray emitters 2.1 to 2.*n* of the sub-arrangements 3.1, 3.2 and the detector 7 are set up such that the X-rays that may be emitted by the X-ray emitters 2.1 to 2.*n*, taken in their entirety, and detected by the detector 7 completely cover the cross-sectional area Q.

However, the region that can be irradiated by a respective one of the sub-arrangement 3.1, 3.2 is restricted by associated collimators 6.1, 6.2 to partial regions Q1, Q2 of approximately the same volume. Here, each collimator 6.1, 6.2 is associated with a sub-arrangement 3.1, 3.2 and thus to a plurality of X-ray emitters 2.1 to 2.*n*.

The partial region Q1 may be irradiated by the sub-arrangement 3.1 and is delimited, as seen in the plane of the drawing that is shown, by first and second straight lines G1, G2 and the margin of the cross-sectional area Q of the region of interest 5. Accordingly, the partial region Q2 is delimited at the margin by the first and second straight lines G1, G2 that are associated with the sub-arrangement 3.2, and the margin of the cross-sectional area Q.

Here, the first straight line G1 that is associated with the sub-arrangement 3.1 are in each case tangent with the margin of the cross-sectional area Q at a lateral marginal points R1. The first straight lines G1 further intersect with first side edges D1 of the detector 7 and run through a first X-ray emitter 2.1 of the sub-arrangement 3.1. The second straight line G2 runs from a further X-ray emitter 2.*n* of the sub-arrangement 3.1, through an upper marginal point R2 that upwardly delimits the cross-sectional area Q, to a second side edge D2 of the detector 7 at the opposite side to the first side edge D1.

The sub-arrangement 3.2 is constructed to be mirror-symmetrical in relation to a center longitudinal axis of the X-ray device 1 such that the second straight lines G2 of the sub-arrangements 3.1, 3.2 intersect at the upper marginal point R2.

The first straight lines G1 of the two sub-arrangements 3.1, 3.2 run almost parallel to one another. In the example shown, the deviation is markedly less than +/−15°.

In a manner not illustrated in more detail, the X-ray emitters 2.1 to 2.*n* have stationary anodes that are made at least partly of tungsten-coated diamond. Further, the stationary anode is embedded in copper.

FIG. 2 shows a further example embodiment of the invention, in which the X-ray emitters 2.1 to 2.*n* are arranged peripherally around a tunnel-like examination chamber 5. The example embodiment of the second example embodiment differs from the first example embodiment shown in FIG. 1 only in that the X-ray emitters 2.1 to 2.*n* are arranged along an arcuate line. In respect of the other features, in particular in respect of the spacings A1, A2 of the X-ray emitters 2.1 to 2.*n* arranged in sub-groups 3.1, 3.2, the reader is referred to the statements relating to FIG. 1.

In a further example embodiment, the X-ray emitters 2.1 to 2.*n* are arranged next to one another and peripherally around the examination chamber 5, as shown in FIG. 2. In addition, further X-ray emitters 2.1 to 2.*n* are arranged in the axial direction, that is to say perpendicular to the plane of the drawing in FIG. 2, the arrangement thereof corresponding to the configuration specified in FIG. 1.

Although the invention has been illustrated and described in detail by means of the preferred example embodiment, the invention is not restricted by the example embodiments shown in the figures. Other variations and combinations may be derived herefrom by those skilled in the art without departing from the scope of protection of the invention.

What is claimed is:

1. An X-ray device for an inverse computed tomography configuration, comprising:
    a plurality of X-ray emitters; and
    a detector arranged opposite the plurality of X-ray emitters, wherein after passing through at least some of a region of interest located in an intermediate region between the plurality of X-ray emitters and the detector, the X-rays emitted by the plurality of X-ray emitters are detectable by the detector, the plurality of X-ray emitters being arranged, in an arrangement other, than equidistant from one another in series, into at least two mutually spaced sub-arrangements, each of the at least two mutually spaced sub-arrangements including a plurality of X-ray emitters, and a spacing between the at least two mutually spaced sub-arrangements being greater than a spacing between adjacent X-ray emitters of at least one of the at least two mutually spaced sub-arrangements, wherein a region irradiatable by the plurality of X-ray emitters of the respective sub-arrangement is limited to a respective partial region, of a plurality of partial regions, of a maximum cross-sectional area of the region of interest that is irradiatable, and wherein the plurality of partial regions, taken in their entirety, completely cover the cross-sectional area of the region of interest.

2. The X-ray device of claim 1, wherein each of the plurality of partial regions is delimited at its margin by a first straight line and a second straight line, wherein the first straight line runs through a side edge of the detector, a lateral marginal point that laterally delimits the cross-sectional area, and an X-ray emitter of an associated respective sub-arrangement, and wherein the second straight line runs through a further, opposite side edge of the detector, an upper marginal point that upwardly delimits the cross-sectional area, and a further X-ray emitter of the associated respective sub-arrangement.

3. The X-ray device of claim 2, wherein the respective second straight lines of the at least two respective sub-arrangements intersect at an upper marginal point.

4. The X-ray device of claim 3, wherein the first straight lines, associated with the at least two respective sub-arrangements, run at an angle of less than 30° to one another.

5. The X-ray device of claim 2, wherein the first straight lines, associated with the at least two respective sub-arrangements, run at an angle of less than 30° to one another.

6. The X-ray device of claim 2, wherein, associated with each respective sub-arrangement, is a respective collimator.

7. The X-ray device of claim 2, wherein the plurality of X-ray emitters grouped in the sub-arrangements are arranged linearly.

8. The X-ray device of claim 2, wherein the X-ray emitters that are grouped in the sub-arrangements are arranged to be equidistant from one another.

9. The X-ray device of claim 2, wherein exactly two sub-arrangements are provided.

10. The X-ray device of claim 2, wherein the plurality of X-ray emitters of the at least two sub-arrangements and the detector are arranged peripherally around a tunnel-like examination chamber.

11. The X-ray device of claim 2, wherein each X-ray emitter of the at least two sub-arrangements includes a stationary anode.

12. The X-ray device of claim 1, wherein, associated with each respective sub-arrangement, is a respective collimator.

13. The X-ray device of claim 1, wherein the plurality of X-ray emitters grouped in the sub-arrangements are arranged linearly.

14. The X-ray device of claim 1, wherein the X-ray emitters that are grouped in the sub-arrangements are arranged to be equidistant from one another.

15. The X-ray device of claim 1, wherein exactly two sub-arrangements are provided.

16. The X-ray device of claim 1, wherein the plurality of X-ray emitters of the at least two sub-arrangements and the detector are arranged peripherally around a tunnel-like examination chamber.

17. The X-ray device of claim 1, wherein each X-ray emitter of the at least two sub-arrangements includes a stationary anode.

18. The X-ray device of claim 17, wherein the stationary anode is made at least partly of diamond and includes a coating of tungsten.

19. The X-ray device of claim 18, wherein the stationary anode is embedded in copper.

20. The X-ray device of claim 17, wherein the stationary anode is embedded in copper.

* * * * *